(12) United States Patent
Karla

(10) Patent No.: US 10,201,552 B2
(45) Date of Patent: Feb. 12, 2019

(54) METHOD OF INCREASING THE BIOAVAILABILITY OF AN HIV DRUG

(71) Applicant: HOWARD UNIVERSITY, Washington, DC (US)

(72) Inventor: Pradeep K. Karla, Washington, DC (US)

(73) Assignee: Howard University DC (US)

( * ) Notice: Subject to any disclaimer, the term of this patent is extended or adjusted under 35 U.S.C. 154(b) by 0 days.

(21) Appl. No.: 14/916,803

(22) PCT Filed: Sep. 5, 2014

(86) PCT No.: PCT/US2014/054367
§ 371 (c)(1),
(2) Date: Mar. 4, 2016

(87) PCT Pub. No.: WO2015/035218
PCT Pub. Date: Mar. 12, 2015

(65) Prior Publication Data
US 2016/0193237 A1    Jul. 7, 2016

Related U.S. Application Data

(60) Provisional application No. 61/874,163, filed on Sep. 5, 2013, provisional application No. 61/970,812, filed on Mar. 26, 2014.

(51) Int. Cl.
| | | |
|---|---|---|
| A61K 31/675 | (2006.01) | |
| A61K 9/06 | (2006.01) | |
| A61K 31/47 | (2006.01) | |
| A61K 45/06 | (2006.01) | |
| A61K 31/4745 | (2006.01) | |
| A61K 31/4985 | (2006.01) | |
| A61K 9/00 | (2006.01) | |

(52) U.S. Cl.
CPC .......... *A61K 31/675* (2013.01); *A61K 9/0034* (2013.01); *A61K 9/06* (2013.01); *A61K 31/47* (2013.01); *A61K 31/4745* (2013.01); *A61K 31/4985* (2013.01); *A61K 45/06* (2013.01)

(58) Field of Classification Search
CPC ...... A61K 31/675; A61K 9/0034; A61K 9/06; A61K 31/47; A61K 31/4745; A61K 31/4985; A61K 45/06
USPC ......................................................... 514/248
See application file for complete search history.

(56) References Cited

U.S. PATENT DOCUMENTS

| | | | |
|---|---|---|---|
| 8,178,123 B2 * | 5/2012 | Pauletti | A61K 9/0034 424/423 |
| 2003/0013731 A1 | 1/2003 | Schellens | |
| 2006/0135438 A1 | 6/2006 | Mitra et al. | |
| 2008/0108703 A1 | 5/2008 | Camenisch et al. | |
| 2008/0269161 A1 * | 10/2008 | Perry | A61K 31/203 514/45 |
| 2010/0234467 A1 | 9/2010 | Ottinger et al. | |

FOREIGN PATENT DOCUMENTS

WO    2007/035515 A2    3/2007

OTHER PUBLICATIONS

PCT International Search Report and Written Opinion of the International Searching Authority dated Dec. 22, 2014 for International Application No. PCT/US2014/054367 (13 pages).

* cited by examiner

*Primary Examiner* — Yevgeny Valenrod
(74) *Attorney, Agent, or Firm* — Fitch, Even, Tabin & Flannery, LLP

(57) ABSTRACT

Methods and compositions are provided for reducing transmission and/or infection of HIV in a subject by increasing the bioavailability of a drug in the subject. The methods and compositions provided herein include an efflux transporter inhibitor and a drug effective for reducing the transmission and/or infection of HIV in a subject. The efflux transporter inhibitor is effective to reduce the efflux of the drug through at least one of P-glycoprotein (Pgp), breast cancer resistant protein (BCRP), and multidrug resistant associated protein 1-9 (MRP1-9).

12 Claims, 9 Drawing Sheets

METHOD OF INCREASING THE BIOAVAILABILITY OF AN HIV DRUG

CROSS-REFERENCE TO RELATED APPLICATIONS

This application is a U.S. national phase application filed under 35 U.S.C. § 371 of International Application Number PCT/US2014/054367, filed Sep. 5, 2014, designating the United States, which claims benefit of U.S. Provisional Application No. 61/874,163, filed Sep. 5, 2013, and U.S. Provisional Application No. 61/970,812, filed Mar. 26, 2014, which are hereby incorporated herein by reference in their entirety.

FIELD

Methods and compositions are described for reducing the risk of HIV transmission and infection in healthy humans. Particularly, the methods and compositions include efflux transporter inhibitors and HIV drugs where the drugs are effective for reducing HIV transmission and infection. The methods and compositions may also be used for pre-exposure prophylaxis, post-exposure prophylaxis, and/or treatment of HIV.

BACKGROUND

Human immunodeficiency virus (HIV) is a lentivirus that cause acquired immunodeficiency syndrome (AIDS), in which progressive failure of the immune systems can allow life-threatening infections to thrive. Infection with HIV occurs through transfer of viral genetic material from infected individual to healthy human cells. HIV primarily infects cells in the human immune system by attaching to the CD4 sites of T-cells and injecting the viral genetic material. In view of the devastating effects of HIV and AIDS, significant research has gone into preventing transmission and new infections while simultaneously treating the infected individuals.

Many pharmacologic compositions have been proposed for reducing HIV transmission and infection as well as for the treatment of HIV. For example, the drug Tenofovir has been widely studied for treatment and pre-exposure prophylaxis/post-exposure prophylaxis of HIV. Travuda (Tenofovir/Emtricitabine) is currently the only FDA approved drug for pre-exposure prophylaxis in high risk uninfected individuals. Standard treatment regimen for post-exposure prophylaxis involves a combination of 2 NRTIs (Nucleoside Reverse Transcriptase inhibitors)+1 PI (Protease inhibitor) or 2 NRTIs+1 NNRTI (Non-Nucleoside Reverse Transcriptase Inhibitor). The effectiveness of current pharmacologic interventions has proven limited and was not proven to completely prevent. HIV transmission.

It is believed that sexual transmission accounts for approximately 90% of HIV infection. Though promising, none of the mucosal microbiocides and/or oral therapies have demonstrated effective protection against the sexual transmission of HIV. In fact, attempts to develop an effective vaginal gel to reduce HIV transmission and infection have not proven fruitful. For example, attempts to incorporate Tenofovir, an NRTI, into a vaginal gel have not proven sufficiently effective for reducing the transmission and/or infection of HIV via sexual transmission.

Tenofovir is an antiretroviral drug belonging to the class of nucleotide analogue reverse transcriptase inhibitors (NRTI), which can block reverse transcriptase, an enzyme crucial for the production of viral genetic material in HIV infected people. Tenofovir is currently employed as a first line treatment option for HIV patients because of good therapeutic potency, low overall toxicity, and dosing convenience. This drug is administered orally in the form of disoproxil ester prodrug, which is deesterified to release the active drug (tenofovir) with a bioavailability of ≥20%. It should be understood that other drugs may also be useful for pre-exposure prophylaxis, post-exposure prophylaxis and/or treatment of HIV.

SUMMARY

Described herein are methods and compositions for increasing the biolavailability of an HIV drug, which may also result in reducing HIV transmission and infection in subjects. Further, the methods and compositions may be used for pre-exposure prophylaxis, post-exposure prophylaxis and/or treatment of HIV. It has been unexpectedly found that human T-cells express multiple ATP binding cassette (ABC) drug efflux transporters, such as Multi Drug Resistance Associated Proteins (MRPs1-9), P-glycoprotein (Pgp) and Breast Cancer Resistance Protein (BCRP), and that these efflux transporters are an important factor in the delivery of HIV drugs. Efflux transporters play an important role in conferring drug resistance by pumping the drug compounds, such as antimicrobials, outside the cell by an energy-dependent mechanism. Further, it was unexpectedly found that human T-cells demonstrated that MRP, Pgp and BCRP are functionally active leading to decreased intracellular concentrations of Tenofovir. A significant increase in intracellular accumulation of Tenofovir was noticed in the human T-cells with the use of specific MRP, BCRP and Pgp inhibitors.

It has been found that inhibition of the drug efflux transporters in human T-cells significantly improves bioavailability of many HIV drugs. The methods and compositions provided herein include an efflux transporter inhibitor in combination with at least one HIV drug, where the combination of the efflux transporter inhibitor and one at least one HIV drug is effective for reducing HIV transmission and/or infection. In this aspect, an efflux transporter inhibitor can be incorporated into a treatment regimen and/or exposure prophylaxis to be used in conjunction with an HIV drug. It has not previously been demonstrated that employing drug efflux inhibition is effective to reduce HIV transmission and/or infection in humans. In one form, employing specific ABC drug efflux pump inhibitors along with an HIV drug can be a highly effective approach for use as a vaginal (mucosal) microbiocide formulation to decrease the sexual transmission of HIV. The use of drug efflux pump inhibitors along with an HIV drug may also be suitable for other applications, such as an oral application, an injectable form and other forms suitable for providing the combination. The use of specific ABC drug efflux pump inhibitors can significantly increase the intracellular HIV drug concentrations in human T-cells leading to enhanced pre-exposure prophylactic effect. The use may also be suitable for post-exposure prophylaxis and/or treatment of HIV.

By one approach, a method is provided for reducing the HIV transmission and/or infection in a subject by increasing the bioavailability of a drug in the subject's T-cells, the method comprising applying a therapeutically effective amount of a drug and an efflux transporter inhibitor, the amount of efflux transporter inhibitor applied in an amount effective to reduce the efflux of the drug in the subject's T-cells. By one approach, the drug and efflux transporter inhibitor are applied topically as a mucosal gel. In one aspect, the subject is a human.

The efflux transporter inhibitor used in the methods and compositions described herein is effective to reduce the efflux of the drug through at least one efflux transporter in human T-cells, such as inhibitors selected from the group consisting of P-glycoprotein (Pgp), breast cancer resistant protein (BCRP), multidrug resistant associated proteins 1-9 (MRP1-9) and combinations thereof. Other suitable inhibitors are also contemplated as discussed herein.

In some approaches, the amount of efflux transporter inhibitor included in the methods and compositions described herein is effective to reduce the efflux of the drug in the subject's T-cells to improve the therapeutic efficacy of the drug when administered in a given quantity. In one form, a two-fold increase in intracellular accumulation of Tenofovir is achieved with the use of efflux pump inhibitors. According to one form, the therapeutic efficacy is expected to be doubled with the use of inhibitors. In another form, a 50% increase in intracellular accumulation of Tenofovir is achieved. According to another form, greater than a 100% increase in intracellular accumulation of Tenofovir is achieved.

In some approaches, the concentration of the efflux transporter inhibitor used is in a range of about 25 µM to about 100 µM. In another approach, the concentration of the efflux transporter inhibitor used is in a range of about 25 µM to about 50 µM. It should be noted that in some forms, excessive loading of efflux transporter inhibitors may be toxic or otherwise impair the function of the cells. In some approaches, the concentration of the HIV drug may be in a range of about 04% to about 2%. However, it should be noted that other concentrations may be used depending on the specific drug and/or efflux transporter inhibitor that is used. In some approaches, the ratio of the efflux transporter inhibitor to the HIV drug is about 1:1 to about 1:100.

Generally, the time between application of the efflux transporter inhibitor and the drug, the relative amounts of the efflux transporter inhibitor and the drug, and the ratio of the efflux transporter inhibitor to the drug are effective to increase the therapeutic efficacy of the drug for reducing HIV transmission and/or infection as compared to administering the same amount of the drug without the efflux transporter inhibitor. In one aspect, the efflux transporter inhibitor is administered before administration of the drug, such as within minutes of administration of the efflux transporter inhibitor. In another approach, the efflux transported inhibitor is administered at the same time as the drug. In yet another approach, the efflux transported inhibitor is administered after administration of the drug.

A composition for reduction of HIV transmission and/or infection in a subject is also described herein. By one approach, the composition comprises an efflux transporter inhibitor and at least one HIV drug, the drug included in a therapeutic amount for reduction of HIV transmission and/or infection. The relative amounts of the efflux transporter inhibitor and the drug, as well as the ratio of the efflux transporter inhibitor to the drug, in the composition are effective for increasing a therapeutic efficacy of the drug for reduction of HIV transmission and/or infection as compared to administering the same amount of the drug without the efflux transporter inhibitor. In one aspect, the drug class is Nucleoside Reverse Transcriptase Inhibitors including, but not limited to Tenofovir, emtricitabine, and the like. In another aspect, the drug classes include Protease Inhibitor (Ritonavir etc.), Non-Nucleoside Reverse Transcriptase Inhibitor (Efavirenz etc.), Integrase inhibitors (Elvitegravir etc.) and Entry inhibitors (Maraviroc etc.). In another aspect, the efflux transporter inhibitor is MRP inhibitor (MK571 and the Pgp inhibitor (Pgp-4008 and the like), BCRP inhibitor and/or (Fumitrimorgin C and the like) and combinations thereof. Other inhibitors and substrates can be used as will be understood from the below description.

These and other aspects may be understood more readily from the following description and the appended drawings.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

DETAILED DESCRIPTION

Figure 1:
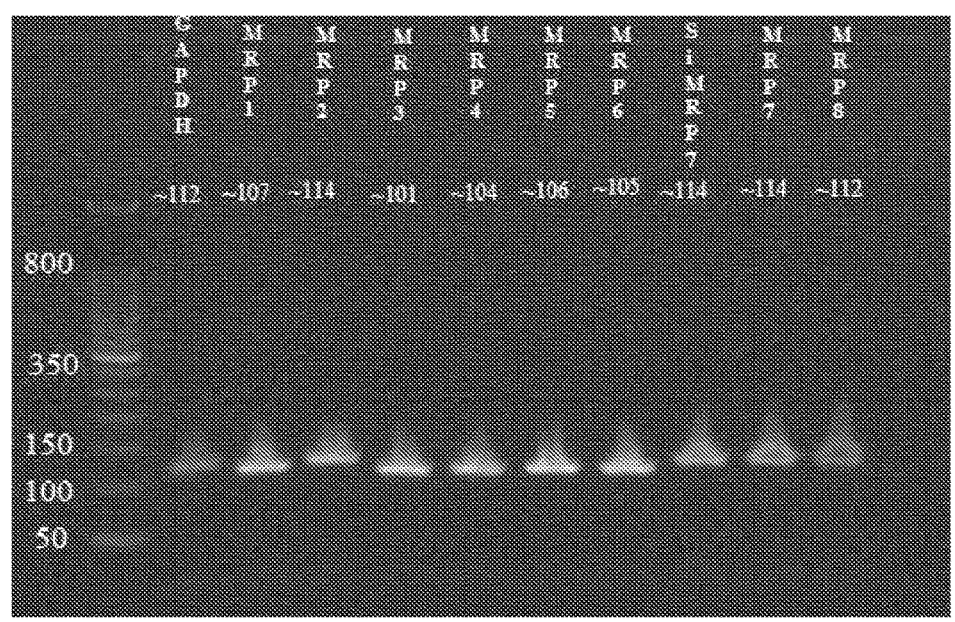
FIG. 1 illustrates RT-PCR gene Expression of MRP's 1-8 drug efflux transporters in Human Vaginal Epithelial Cells.

Described herein are methods and compositions for reducing HIV transmission and/or infection in a subject by increasing the bioavailability of a HIV drug by modulating the efflux of the drug in the subject, such as at a site specific location. The methods and compositions may also be suitable for post-exposure prophylaxis and/or treatment of HIV. In one form, the bioavailability of the drug is increased via a vaginal mucosal microbiocide. In other forms, the bioavailability is increased in other human T-cells. It has been discovered that there are significant benefits in drug efficacy, and also treatment of certain diseases, by incorporating drug efflux transporter modulators in compositions and/or treatment regimens. In some approaches, modulation of the efflux transporters is by inhibition. It has been found that inhibition of the drug efflux transporters in human T-cells can significantly improve bioavailability of many HIV drugs, thereby significantly increasing the therapeutic efficacy of the HIV drug. Conventional mucosal treatments do not involve use of efflux transporter inhibitors in conjunction with other medicaments.

Efflux transporters identified in human T-cells include P-glycoprotein (Pgp), breast cancer resistant protein (BCRP), and multidrug resistant associated proteins 1-9 (MRPs 1-9). The presence of these efflux transporters in T-cells has been found to confer drug resistance to a variety of topically applied drugs. The presence of MRPs, Pgp and BCRP efflux pumps in T-cells imply the likelihood of drug resistance to a wide range of drugs, such as HIV drugs. Efflux pumps can also act in an additive manner to efflux a wider range of drug molecules, forming a very strong physical barrier for HIV drug delivery.

Pgp belongs to the ATP-binding cassette (ABC) family of transporters which use ATP as an energy source. This efflux transporter has two transmembrane sites embedded in the lipid bilayer of the cell membrane. Each transmembrane site includes six transmembrane domains. Pgp has two nucleotide binding domains which are also known as ATP binding domains.

MRPs appear to play a role in drug efflux and the resulting decrease in drug efficacy. MRPs are also classified in the ABC family of transporters and require ATP for efflux function. The major structural difference between MRPs and Pgp is the presence in MRPs of an additional transmembrane site in the lipid bilayer, which includes five transmembrane domains. Additionally, another significant difference between the two transporters is the presence in MRP of an amino terminal on the external side of cell membrane.

BCRP also primarily employs ATP for its efflux function. BCRP is referred to as a "half transporter" and has one transmembrane site and one ATP binding site. The transmembrane site has six transmembrane domains embedded in the lipid bilayer.

Human immunodeficiency virus (HIV) is a lentivirus that cause acquired immunodeficiency syndrome (AIDS), in which progressive failure of the immune systems can allow life-threatening infections to thrive. Infection with HIV occurs through transfer of certain bodily fluids. HIV infects cells in the human immune system such as CD4 sites of T-cells. For example, attachment of gp120 site of HIV to the CD4+ T-cells, incorporation of viral enzymes and genetic material constitute the first steps of HIV infection.

By one approach, a method is provided for reducing HIV transmission and/or infection in a subject in need thereof by increasing the bioavailability of a drug in the subject, such as in the vaginal mucosa. In one approach, the method is suitable for post-exposure prophylaxis and/or treatment of HIV in human T-cells. In one form, the method comprises applying a therapeutically effective amount of a drug and an efflux transporter inhibitor to the subject's vaginal mucosa, the efflux transporter inhibitor applied in an amount effective to reduce the efflux of the drug in the subject's T-cells as compared to using the same drug in the same amount but without the efflux transporter inhibitor. By one approach, the drug and efflux transporter inhibitor are applied topically, such as in the form of a vaginal gel. The method and composition may also be incorporated into other T-cells such as via an oral dose, an injectable dose and other forms. In one aspect, the subject is a human.

In one particular aspect, the efflux transporter inhibitor is cyclosporine A. According to another form, the efflux transporter inhibitor is selected from the group consisting of MK571, Fumitrimorgin C, Pgp-4008. According to one form, the efflux transporter inhibitor is MRP inhibitor (MK571 and the like), Pgp inhibitor (Pgp-4008 and the like), BCRP inhibitor and/or (Fumitrimorgin C and the like) and combinations thereof. Other inhibitors and combinations of inhibitors may be used in combination with the drugs. In one form, the drug comprises at least one material selected from the drug class Nucleoside Reverse Transcriptase Inhibitors including, but not limited to Tenofovir, emtricitabine, and the like, a Protease Inhibitor (Ritonavir etc.), a Non-Nucleoside Reverse Transcriptase Inhibitor (Efavirenz etc.), an Integrase inhibitors (Elvitegravir etc.), Entry inhibitors (Maraviroc etc.) and combinations thereof. In one aspect, the drug is Tenofovir. In one aspect, the subject is a human.

By one approach, the time between application of the efflux transporter inhibitor and the drug, the relative amounts of the efflux transporter inhibitor and the drug, and the ratio of the efflux transporter inhibitor and the drug are effective to increase the therapeutic efficacy of the drug for treating the HIV as compared to administering the same amount of the drug without the efflux transporter inhibitor. In one form, an HIV drug, such as Tenofovir, may be used in a variety of ratios.

At least in some approaches, the drug and efflux transporter inhibitor are applied as a vaginal gel at substantially the same time. By "substantially the same time" is meant within about 10 minutes, in another aspect within about 5 minutes, in another aspect within about 1 minute, and in another aspect within about 0.5 minutes.

As used herein, the term "treating" refers to an intervention performed to alter the pathology of, and thereby substantially alleviate or reduce in severity, transmission and/or infection of HIV. As used herein, the term "subject" includes mammals and specifically humans. Accordingly, "treating" refers to both therapeutic treatment and prophylactic measures. The related term "treatment," as used herein, refers to the act of treating a symptom, disease or condition.

As used herein, the term "transmission" refers to the passing of a communicable disease from a host to another subject who may be uninfected. The transmission can be indirect and/or direct, such as via sexual transmission or other forms of transmission.

As used herein, the term "infection" refers to invasion of a host organism's bodily tissues by a disease causing organism, their multiplication and/or the reaction of the host's tissues to the organisms and the toxins they produce.

As used herein, the terms "therapeutically effective amount" or "effective amount" refer to the amount of drug and/or efflux transporter modulator required to confer a biological or meaningful patient benefit, such as the biological or medical response or improvement sought by a medical doctor or other medical professional. In one aspect, the terms "therapeutically effective amount" or "effective amount" are intended to mean the amount of drug and/or efflux transporter modulator that will bring about a biologically meaningful reduction in the transmission and/or infection of the subject. Doses that exhibit large therapeutic indices are preferred. Effective amounts may vary, as recognized by those skilled in the art, depending, for example, on route of administration, dosage form, inclusion of additional active agents, as well as age, weight, sensitivity, and health of the subject.

In some approaches, the concentration of the efflux transporter inhibitor used is in a range of about 25 µM to about 100 µM. In another approach, the concentration of the efflux transporter inhibitor used is in a range of about 25 µM to about 50 µM. It should be noted that in some forms, excessive loading of efflux transporter inhibitors may be toxic or otherwise impair the function of the cells. In some approaches, the concentration of the HIV drug may be in a range of about 0.1% to about 2%. However, it should be noted that other concentrations may be used depending on the specific drug and/or efflux transporter inhibitor that is used. In some approaches, the ratio of the efflux transporter inhibitor to the HIV drug is about 1:1 to about 1:100.

In some approaches, the concentration of the drug is more than, less than or the same as standard HIV drug treatment concentrations, dosages and treatment protocol.

As used herein, the term "efflux transporter inhibitor" means a chemical compound, protein, peptide, or other molecule that is effective to stop or reduce extrusion of a drug outside the cell via at least one efflux transporter in the subject. In some approaches, the efflux transporter inhibitor is effective to stop or reduce extrusion of a drug via at least one efflux transporter selected from the group consisting MRPs, BCRP, and Pgp such as of the vaginal epithelium.

Examples of efflux transporter inhibitors include, for example, MK-571 ($C_{26}H_{26}ClN_2O_3S_2$.Na; a specific MRP inhibitor sold by Biomol International L. P. (PA, USA)), ketoconazole (a specific Pgp inhibitor), GF120918 (a specific Pgp inhibitor marketed as Elacridar by Santa Cruz Biotechnology) indomethacin, PGP-4008, bimatoprost (marketed as LUMIGAN® by Allergan), latanoprost (marketed as XALATAN® by Pfizer), sulfinpyrazone (a MRP5 modulator), and cylosporin-A (a Pgp inhibitor marketed as RESTASIS® by Allergan). Advantageously, cyclosporine-A may be used in the methods and compositions described herein. Very strong substrates for the efflux transporters can act as inhibitors. Therefore, additional efflux transporter inhibitors can be designed and identified by one of ordinary skill in the art.

It has been found that efflux transporters (such as MPR and Pgp) sometimes act in conjunction to efflux certain drugs, and the combined activity of the efflux transporters forms a strong physical barrier against HIV drug delivery on human T-cells. In some approaches, use of a combination of efflux transporter inhibitors can result in an at least additive increase in uptake of drugs. While not wishing to be limited by theory, it appears that BCRP and Pgp along with MRPs play a role in drug efflux of NRTI class of HIV drugs. Also not wishing to be limited by theory, it is presently believed that MRP4/MRP5 transporters play a significant role in the efflux of nucleoside and nucleotide analogues (NRTIs). It has also been demonstrated that efflux inhibitor GF120918 interacts with both BCRP and Pgp.

In one aspect, the efflux transporter inhibitor is applied in an amount effective to reduce the efflux of the drug through the subject's T-cells for a period of time sufficient for the administered drug to have clinical benefit to the patient.

As used herein, "drug" comprises at least one active ingredient, including, for example, compound, protein, peptide, or prodrug compound, that is effective to ameliorate or reduce transmission and/or infection of HIV. In one aspect, the efficacy of the drug is substantially increased when used in conjunction with an efflux transporter inhibitor. In one aspect, the drug is a substrate of at least one efflux transporter selected from the group consisting of MRPs, BCRP, and Pgp, in some approaches, the active ingredient includes at least one of NRTIs, PI, NNRTIs and combinations thereof. In one form, the active ingredient includes at least Tenofovir. Other drugs, active ingredients and the like may include compositions such as integrase inhibitors, fusion inhibitors, entry inhibitors and the like.

In some approaches, the methods and/or compositions described herein may further include a second active ingredient in addition to the first active ingredient and efflux transporter inhibitor. In one aspect, the second active ingredient may include, for example, a steroid or anti-inflammatory agent. Steroids useful in the methods and compositions described herein include, for example, hydrocortisone, fluromethalone (FML), fluromethalone acetate (FLAREX®), prednisolone sodium phosphate marketed as Predsol), prednisolone acetate (PRED FORTE®), and dexamethasone (MAXIDEX™). The second active ingredient can be provided in the same or different drug as the first active ingredient.

By some approaches, the drug can include both a first and a second active ingredient. By other approaches, it is contemplated that the first and second active ingredients are provided in separate compositions and are separately applied to the subject.

In one aspect, the composition may be applied directly to a target tissue, in one aspect the subject's vaginal mucosa, or to a surrounding fluid or tissue. By some approaches, administration to the desired location may be by topical application. In other aspects, the composition can be administered in other acceptable methods, such as an oral dose, injectable dose and the like. The dosage form can vary depending on the desired effect as a pre and/or post exposure prophylaxis and the location of the intended effect.

The composition can be prepared in a variety of forms. For example, a liquid formulation can be prepared, such as, for example, in the form of a solution, emulsion, or suspension in a non-toxic, pharmaceutically-acceptable carrier. In another aspect, a gel formulation can be prepared, such as a vaginal gel. In some forms, the efflux transporter inhibitor and/or active ingredients, such as HIV drugs, can be combined with a carrier. Such carriers include thermoreversible gels and the like. These carriers may be in a form such that when they are administered to a subject, such as in the form of a mucosal administration, the combination is in the form of a gel.

In another aspect, the drug may be a powder or lyophilisate that is reconstituted with a solvent prior to use. In yet another aspect, the formulation may be in the form of an emulsion or liquid concentrate that is suitable for dilution prior to administration. Exemplary pharmaceutically-acceptable carriers include saline, buffered saline, isotonic saline, Ringer's solution, dextrose, sterile water, deionized water, glycerol, ethanol, 5% dextrose in water, and combinations thereof.

The composition may comprise a variety of optional ingredients. For example, the topical formulation may include ingredients such as but not limited to preservatives, lubricant, stabilizer, colorant, diluent, isotonic agent, pH modifier, buffer, excipient, and the like and additional active ingredients, if desired. In one aspect, any additional ingredients included in the composition should not negatively impact the stability of the active ingredient(s) in the drug.

The use and/or treatment regimen can vary depending on the particular needs of the subject. By way of non-limiting illustration, the combination of drug and efflux transporter inhibitor may be applied at least once daily. By another approach, the combination of drug and efflux transporter inhibitor may be applied at least twice a day. A shorter or longer treatment regimen may be used, if desired.

In one form, the site specific application of one or both of the inhibitor and the drug may provide for a more concentrated dosing of the drug in a desired area. If the inhibitor and the drug are applied more generally, such as via an injection, the inhibitor and drug may become more dilute in the bloodstream and may not provide an adequate dosage in a desired area. Instead, by using the inhibitor and drug in a form that can be applied to a specific location, such as in the form of a vaginal gel, it is possible to provide a more concentrated dosage in the desired area. In this form, the inhibitor and drug may be suitable to reduce the transmission and/or infection of HIV through sexual transmission.

Advantages and embodiments of the method and compositions described herein are further illustrated by the following example; however, the particular conditions, processing schemes, compositions, and amounts thereof recited in these examples, as well as other conditions and details, should not be construed to unduly limit this method. All percentages are by weight unless otherwise indicated. All references listed herein are incorporated herein by reference in their entireties.

EXAMPLES

Figure 2:
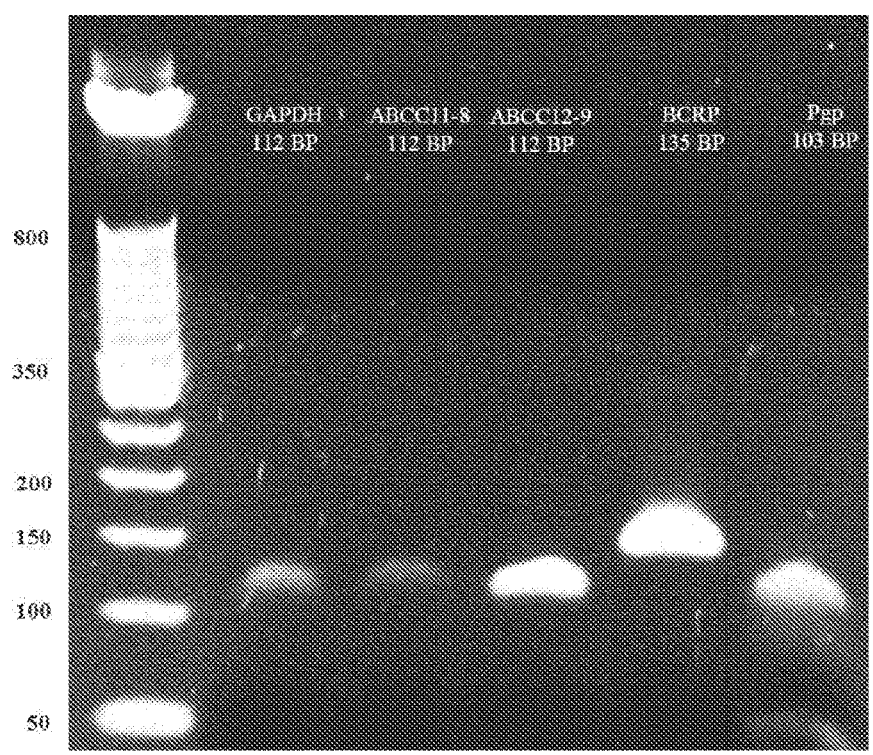
FIG. 2 illustrates RT-PCR gene Expression of MRP8, MRP9, BCRP and Pgp drug efflux transporters in Human Vaginal Epithelial Cells.
Figure 3:
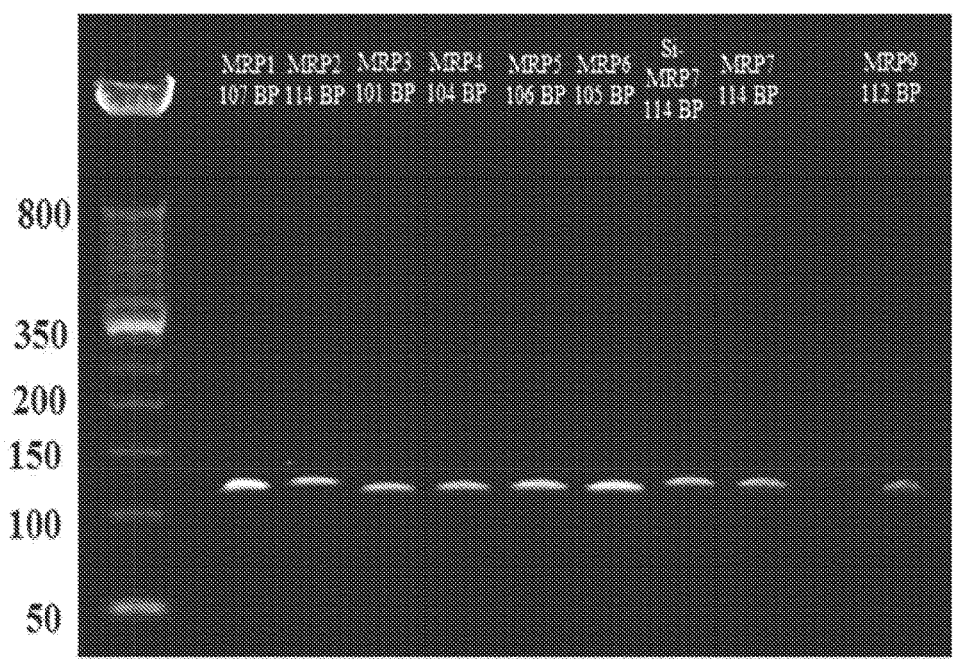
FIG. 3 illustrates RT-PCR gene Expression of MRP's 1-7 and MRP9 drug efflux transporters in Unactivated Human T-Cells.
Figure 4:
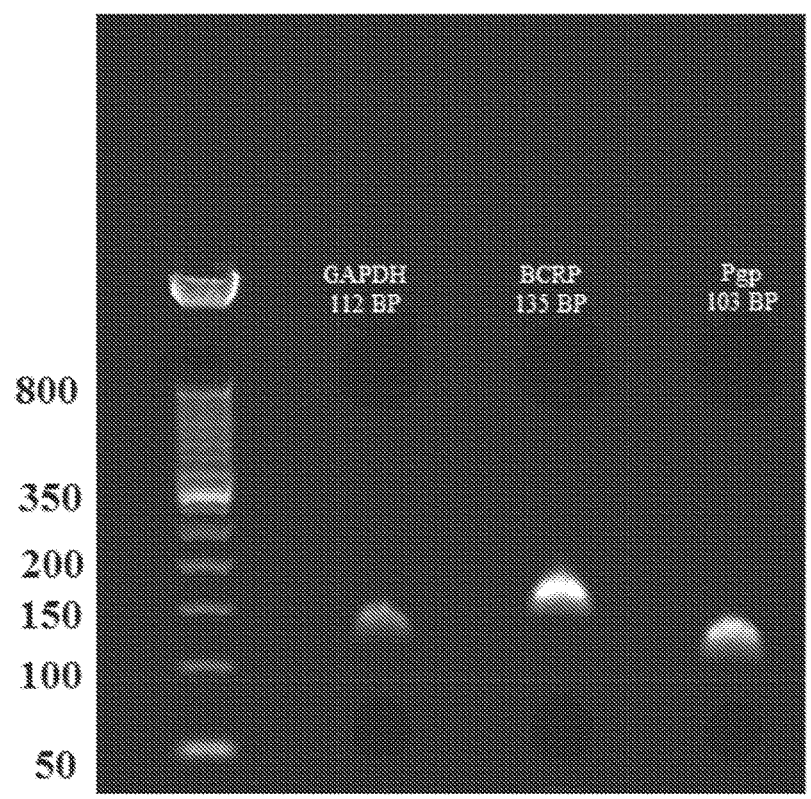
FIG. 4 illustrates RT-PCR gene Expression of BCRP and Pgp drug efflux transporters in Unactivated Human T-Cells.
Figure 5:
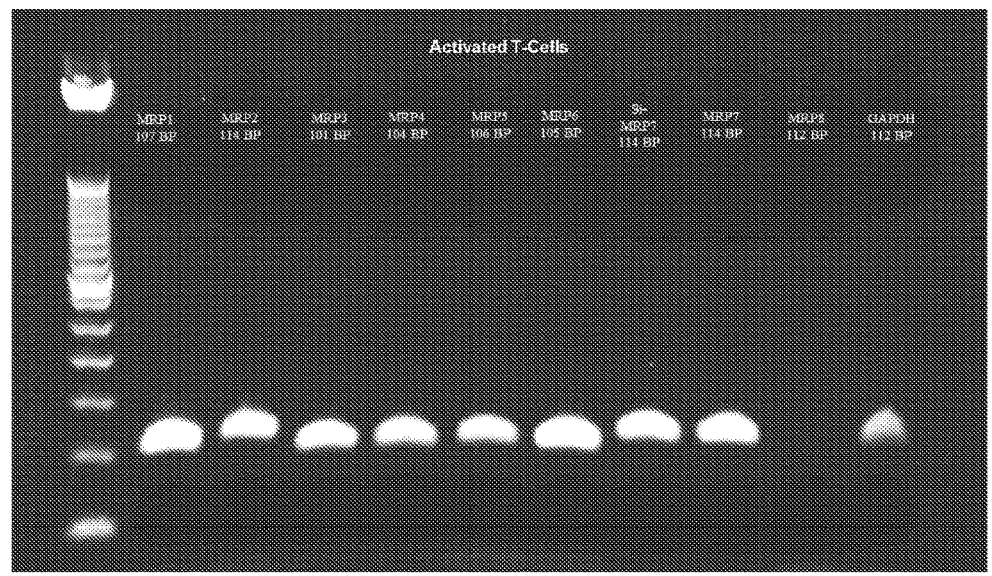
FIG. 5 illustrates RT-PCR gene Expression of MRP's 1-8 drug efflux transporters in Unactivated Human T-Cells.
Figure 6:
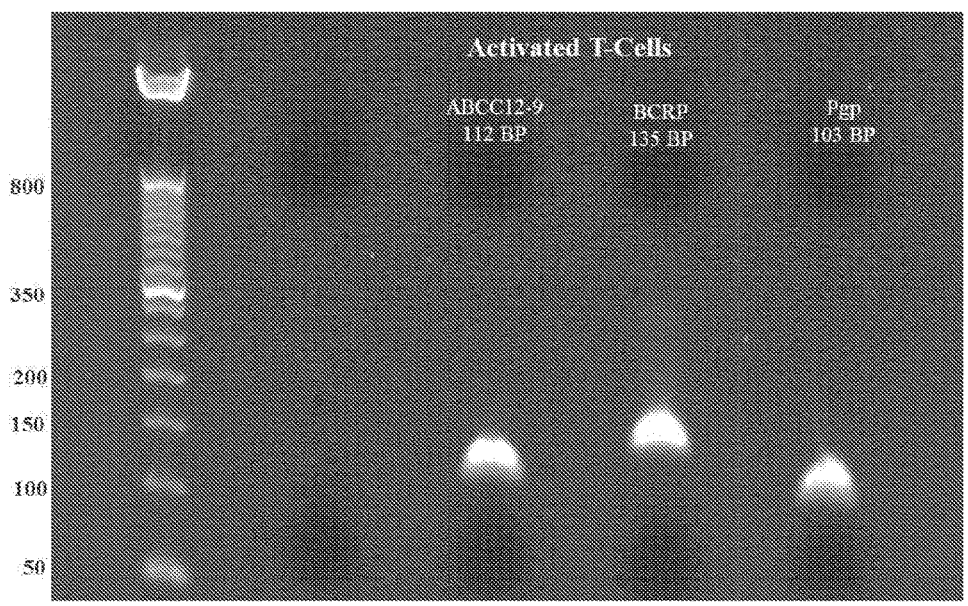
FIG. 6 illustrates RT-PCR gene Expression of MRP9, BCRP and Pgp drug efflux transporters in Unactivated Human T-Cells.

FIGS. 1-6 illustrate various efflux transporters in human cells. For example, FIG. 1 illustrates RT-PCR gene Expression of MRP's 1-8 drug efflux transporters in Human Vaginal Epithelial Cells. FIG. 2 illustrates RT-PCR gene Expression of MRP8, MRP9, BCRP and Pgp drug efflux transporters in Human Vaginal Epithelial Cells. FIG. 3 illustrates RT-PCR gene Expression of MRP's 1-7 and MRP9 drug efflux transporters in Unactivated Human T-Cells. FIG. 4 illustrates RT-PCR gene Expression of BCRP and Pgp drug efflux transporters in Unactivated Human T-Cells. FIG. 5 illustrates RT-PCR gene Expression of MRP's 1-8 drug efflux transporters in Unactivated Human T-Cells. FIG. 6 illustrates RT-PCR gene Expression of MRP9, BCRP and Pgp drug efflux transporters in Unactivated Human T-Cells.

Figure 7:
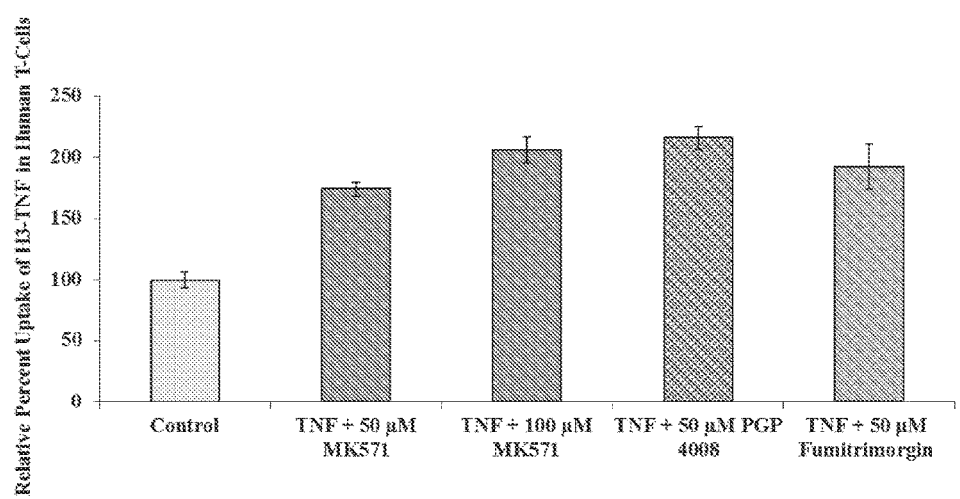
FIG. 7 illustrates Tenofovir uptake in Unactivated Human T-Cells in the presence and absence of specific MRP, Pgp and BCRP efflux transporter inhibitors.

As shown in FIG. 7, uptake of radio labeled Tenofovir was evaluated in the presence and absence of specific. ABC efflux pump inhibitors. Briefly, human T-cells in the culture media (1 million/mL) were transferred to 15 mL centrifuge tubes. Radio labeled Tenofovir was added to the control tube and radio labeled Tenofovir along with defined concentrations of efflux pump inhibitors were added to the treatment tubes. The tubes were incubated for 15 minutes under culture conditions (37° C., 5% $CO_2$/95% relative humidity). Following incubation, the tubes were centrifuged at 2000 rpm for 15 min and the supernatant is discarded. Ice cold stop solution (210 mM KCl, 2 mM HEPES [pH 7.4]) was added to stop the reaction. The cells were resuspended in stop solution to ensure washing and centrifuged at 2000 rpm for 15 min. The treatment with stop solution, washing and centrifugation is repeated to ensure through washing. 1 mL lysis solution (0.3 M NaOH, 0.1% Triton X-100) was added to the cell pellet and samples and incubated overnight to ensure complete cell lysis. Intracellular concentrations were analyzed by Beckman LS 6500 automated Scintillation Counter. The results of the various samples are shown in FIG. 7.

Figure 8:
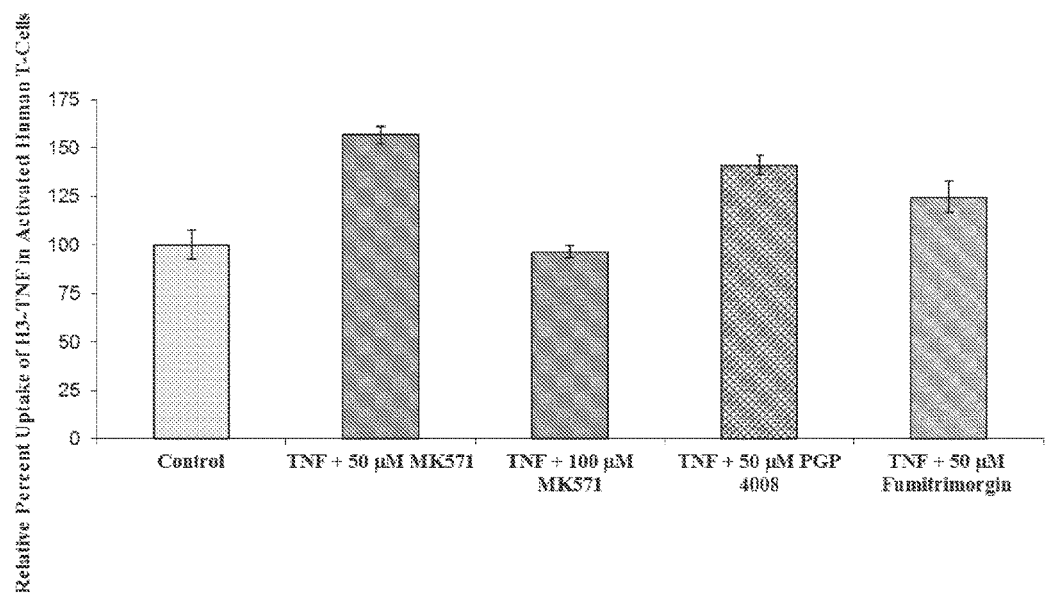
FIG. 8 illustrates Tenofovir uptake in activated Human T-Cells in the presence and absence of specific MRP, Pgp and BCRP efflux transporter inhibitors.
Figure 9:
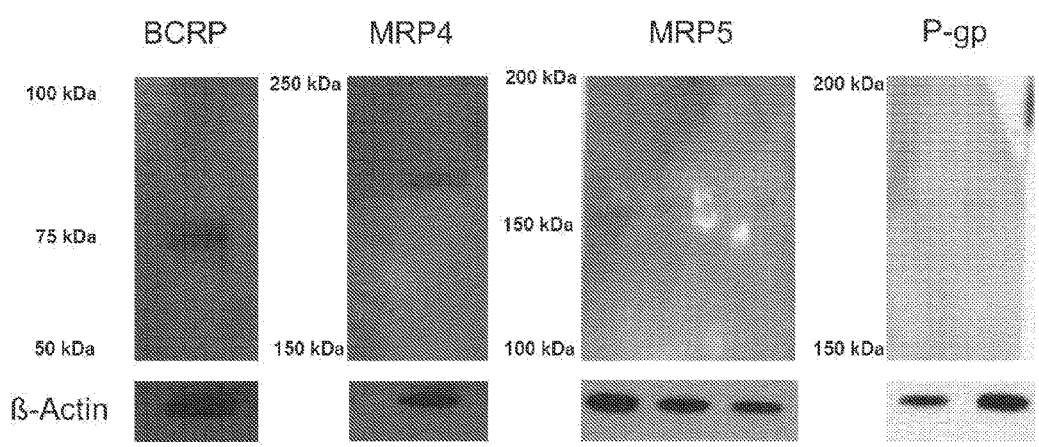
FIG. 9 illustrates western blot analysis showing expression of BCRP, MRP4, MRP5 and Pgp at the protein level in human T-cells.

As shown in FIG. 8, Tenofovir uptake in activated Human T-Cells in the presence and absence of specific MRP, Pgp and BCRP efflux transporter inhibitors was analyzed. The unactivated human T-cells were activated by treatment with (5 microg/ml PHA+20 U/ml IL-2) for 48 hrs. The intracellular uptake of Tenofovir in the presence and absence of ABC drug efflux pump inhibitors was performed by employing the same protocol and drug/inhibitor compositions described above for FIG. 7. The results of the activated human T-cells are shown in FIG. 8.

In the unactivated T-cells, a concentration of 50 µM inhibitors resulted in a significant intracellular concentrations. In the activated T-cells the cells appeared to be sensitized after activation and a lower inhibitor concentration seems appropriate. It is hypothesized that in certain concentrations, some inhibitors may have a toxic effect on the T-cells.

Use of Nanoparticles

HIV drugs, such as Tenofovir, may also be prepared and used in a nanoparticle form. In this regard, it is believed that such drugs, when prepared in a nanoparticle form, may increase the uptake of the drug. Therefore, the nanoparticle form may be used with or without efflux transporter inhibitors, as will be understood from the below description.

PLGA is an FDA-approved biodegradable copolymer widely used in the preparation of pharmaceutical nanoformulations. Nanoparticles can enable site specific delivery by size dependent uptake by affected cells and improve the drug efficacy by providing a sustained drug release. In one form, PLGA can be used for encapsulating HIV drugs, such as tenofovir. In one form, thermoreversible nano gel formulation may be formulated to be in solution form at refrigerating conditions (2-8° C.) and transform into a gel matrix when exposed to vaginal body temperature (≥34° C.).

Preparation of TFR Loaded PLGA Nanoparticles by Solvent Diffusion

In one form, a solvent diffusion method may be adapted from a published protocol with modifications to form the nanoparticles. (Xu A., Yao M., Xu G., Ying J., Ma W., Li B., Jin Y. A physical model for the size-dependent cellular uptake of nanoparticles modified with cationic surfactants, International Journal of Nanomedicine, July 2012, Vol. 7, pp. 3547-3554.) Briefly, TFR (10-100 mg) and the polymer (100-400 mg), PLGA were co-dissolved in 5 ml DMSO. The organic phase was added drop wise (2 ml/min.) to aqueous phase, containing Triton X 100, under homogenization at 4000-5000 rpm for 30 min. (Power Gen 1000, Fisher Scientific, USA). The suspension was ultrasonicated for 5-10 minutes (Misonix Ultrasonicator (QSonic LLC., USA) and ultra-centrifuged at 15000 rpm for 90 min (Beckman L8-70 M Ultra-centrifuge, Brea, Calif., USA) to collect NPs and then thoroughly washed two times with distilled water to remove the surfactant. Settled pellet was re-suspended in distilled deionized water and tested for particle size and surface morphology by DLS and SEM respectively.

Preparation of LFR Loaded PLGA Nanoparticles by Emulsification-Solvent Evaporation In one form, an emulsification-solvent evaporation method may be adapted from a published protocol with modifications. (Pradhan R., Poudel B. K., Ramasamy T., Choi H. G., Yong C. S., Kim J. O., Docetaxel-loaded polylactic acid-co-glycolic acid nanoparticles: formulation, physicochemical characterization and cytotoxicity studies, Journal of Nanoscience and Nanotechnology, August 2013, Vol. 13(8), pp. 5948-5956.) Briefly, PLGA (75:25) was dissolved in ethyl acetate and added to an aqueous phase containing Pluronic® F68 and TFR to prepare the primary emulsion followed by ultrasonication (Pulse: 0.9/0.1; amplitude 30-35%) for 5 minutes on ice batch. Primary emulsion was added to secondary aqueous phase (2% w/v PVA solution), ultrasonicated for 5 minutes followed by ethyl acetate evaporation at Buchi Rota vapour R-205, USA. The nanoparticles were then separated by ultracentrifugation and the supernatant is discarded. The settled pellets washed with water to remove traces of surfactant than collected in a lyophilization vial and lyophilized at −50° C. for 24-48 h. The particle size was analyzed before lyophilization.

Preparation of Thermo Reversible Buffered Gel Containing PLGA Nanoparticles

In one form, a thermo reversible buffered gel may be prepared based on published protocols with modifications. (Date A. A., Shibata A., Goede M., Sanford B., La Bruzzo K., Beishan M., Destache C. J., Development and evaluation of a thermosensitive vaginal gel containing raltegravir+ efavirenz loaded nanoparticles for HIV prophylaxis, Antiviral Research, December 2012, Vol. 96(3) pp. 430-436; Bilensoy E. M., Abdur Rouf M., Vural I., Şen M., Hincal A. A., Mucoadhesive, Thermosensitive, Prolonged-Release Vaginal Gel for Clotrimazole: β-Cyclodextrin Complex, AAPS Pharm Sci Tech, June 2006, Vol. 7(2), pp. E1-E7.) Poloxamer 407 (Poly(ethylene glycol)-block-poly(propylene glycol-block-poly(ethylene glycol) (20% w/v) was added to pH 4.2 citrate buffer (0.05 M, Citric Acid, Anhydrous 0.5525% w/v, Sodium Citrate, Dihydrate 0.6246% w/v) and stored at 2-8° C. temperature for 24 hour for complete dissolution. A clear liquid solution of polymer composite was obtained. Freeze dried TFR loaded PLGA nanoparticles (Batch No. PGDE3) of predetermined weights were added to obtain a thermoreversibie nano gel formulation with desired drug loading efficiency. The formulation was stored at 4° C. for further use.

Gelling, point was determined by TA Instruments Trios Version: 3.0.2.3156. Sample was scanned between 4° C. to 42° C. with ramp rate 1.0° C./min. Solution was tested at different temperature and shear rate 0.1 to 600l/s.

Particle Size Determination

The particles size and distribution of TFR loaded PLGA nanoparticles were measured by DLS employing Brookhaven 90 Plus DLS and Zetapotentiometer (Brookhaven Instruments Corporation, USA) at room temperature (25° C.). Particles size was represented as an effective diameter in nm.

Morphology

The micro scaled image of nanoparticles was taken by JEOL JSM-7600F Scanning Electron Microscope (JEOL USA Inc., USA). The lyophilized powder was sprinkled on a carbon tap stick stub, coated with gold and focused under a vacuum at 5 KV. The focused images were captured at different magnifications.

Encapsulation Efficiency (EE) and Drug Loading (DL)

EE and DL were determined by RP-HPLC method employing Schimadzu SCL-10AVP Automated HPLC System with Photo Diode Array Detector (Schimadzu Corporation, USA). 10 mg of lyophilized TER loaded PLGA nanoparticles were dissolved in 2-ml ethylacetate. To the solvent mixture, 1 ml HPLC water was added and ultrasonicated for 1 min. for drug extraction and dissolution. Solvent was then evaporated by stirring overnight at room temperature. The sample was filtered by 0.22 μm Durapore (PVDF) membrane filter and the filtrate was analyzed by HPLC. The TFR drug concentrations were estimated from the resultant peak AUC values. The % EE and % DL were calculated with the following formulas:

% Drug loading=(Drug in nanoparticles/Weight of nanoparticles)×100

% Encapsulation efficiency=(Total drug in nanoparticles/Total drug taken)×100

In Vitro Drug Release from PLGA Nanoparticles Dispersed in Buffered Gel

In vitro drug release of TFR from thermo reversible buffered gel containing PLGA nanoparticles was performed for 24 h in Simulated Vaginal fluid type 1 (SVF). 5 ml thermoreversible buffered gel containing 50 mg of Batch No. PGDE3 (PLGA nanoparticles loaded 159.5 μg TFR) was added to 20 ml SVF in a 50 ml tube. The tube is then placed on a Max Q4000 temperature controlled orbital shaker (Thermo Fisher Scientific, USA) at 37° C. with an agitation speed of 60 rpm. At predetermined time intervals, 1 ml of release medium was collected for analysis and replaced with fresh medium to maintain experimental homeostasis. The amount of drug released was measured by RP-HPLC at 260 nm. The samples were filtered by syringe driven Durapore (PVDF) 0.22 μm membrane filter before injecting in to HPLC. Mobile phase consisted of acetonitrile/ 50 mM sodium phosphate buffer pH 5.12 at a ratio of (2.5:97.5; v/v). The flow rate was 1 ml/min. and injection volume was 20 μl. Excellent linearity ((r2 0.99) was obtained from standard curve analysis (2-10 μg/ml).

In initial development phase with experimental trials, two different methods were applied for preparation of PLGA nanoparticles with TFR. In first method (Solvent diffusion) effective particle diameter of nanoparticles without drug (blank) and with drug (TFR) were 94.3-137 nm (PGSD1, PGSD3) and 207.8-228.2 nm (PGSD4, PGSD2) respectively with a narrow size distribution profile. The drawback observed with this method was poor encapsulation of TFR. Drug peak was detected in HPLC but it was below quantification level. This low drug encapsulation was not favorable for the final formulation. A plausible explanation for poor encapsulation with solvent diffusion method is the redistribution of TFR towards the aqueous phase during the mixing phase. Another reason can be that Triton X 100 being a strong surfactant is preventing effective TFR encapsulation. Though the use of Triton X 100, a non-ionic surfactant seems to effectively reduce the particle size and poly dispersity index (PDI), a potential pitfall (poor drug encapsulation) was observed. Ideally, better encapsulation is required with narrow size of nanoparticle for efficient drug delivery system. There is no significant of less nano size of particles if they are not able to carry effective concentration of drug at delivery site.

Second method (emulsification-solvent evaporation) was applied to improve the encapsulation of TFR with PLGA nanoparticles. With this method particles size was increased as compared to solvent diffusion. Different concentration of Pluronic F68 (0.2% to 1% w/v of non-aqueous phase) was used to reduce the particles size. In two exemplary attempts, particle size was observed 298 nm and 300 nm respectively. No significant different in particles size was created when concentration of Pluronic F68 increased from 0.6% to 1% w/v. During preparation of PLGA nanoparticles it was observed that globules size reduced in primary emulsion phase and it was not stable but after dilution with further secondary aqueous phase became quite stable. Hardening of particles was occurred in solvent evaporation step. PDI was increased from 0.131 to 0.237 nm (Table 1).

TABLE 1

Batch variables and physiochemical parameters of PLGA nanoparticles.

| Batch No. | PLGA conc. (mg) | TFR (mg) | Triton X100 (ml) | Pluronic® F68 (% w/v) | Total Sonication time (min.) | Particle size (nm) ±SE | PDI ± SE | EE (%) | DL (%) | Zeta Potential (mV) mean ± SE |
|---|---|---|---|---|---|---|---|---|---|---|
| PGSD1 | 100 | 0 | 0.5 | 0 | 10 | 97.8 ± 0.2 | 0.054 ± 0.005 | †Blank | †Blank | −4.58 ± 0.56 |
| PGSD2 | 100 | 10 | 0.5 | 0 | 10 | 228.2 ± 1.7 | 0.143 ± 0.018 | *NQ | *NQ | −4.05 ± 1.02 |
| PGSD3 | 400 | 0 | 0.5 | 0 | 10 | 137.1 ± 0.4 | 0.062 ± 1.7 | †Blank | †Blank | −5.45 ± 0.96 |
| PGSD4 | 400 | 10 | 0.5 | 0 | 10 | 207.8 ± 3.8 | 0.110 ± 0.019 | *NQ | *NQ | −5.06 ± 1.12 |
| PGDE1 | 100 | 0 | 0 | 0.2 | 10 | 278.6 ± 5.3 | 0.131 ± 0.026 | †Blank | †Blank | −5.86 ± 0.41 |
| PGDE2 | 100 | 10 | 0 | 0.2 | 10 | 413.6 ± 8 | 0.237 ± 0.008 | 10.78 | 1.18 | −6.32 ± 0.67 |
| PGDE3 | 400 | 100 | 0 | 0.6 | 10 | 298 ± 3.9 | 0.217 ± 0.011 | 1.18 | 0.31 | −6.53 ± 0.07 |
| PGDE4 | 400 | 100 | 0 | 1 | 10 | 300 ± 0.8 | 0.209 ± 0.08 | 1.43 | 0.42 | −6.76 ± 0.61 |

*NQ: Not quantify (drug was below limit of quantification by HPLC), †Blank: Placebo (Batch PGSD1, PGSD3, PGDE1), Zeta potetnial of PureTenofovir solution (0.68 ± 1.25), SE: standard error, TFR: Tenofavir, PDI: Polydispersity index, EE: Enapsualtion efficiency, DL: Drug loading.

Simultaneously, with this method, the encapsulation and drug loading efficiencies were obtained in the ranges of 1.43-10.78 and 0.25-1.18%, respectively. In Table 1, % EE did not significantly change with variations in drug concentrations (10 mg to 100 mg) and polymer (400 mg).

The thermoreversible gel prepared with Poloxamer 407 (20% w/v) and it was analyzed for gelling point. When a solution was scanned from 4° C. to 27.5° C., a rapid increase of viscosity was observed at 25° C. and converted into gel. Below 15° C., the sample was in solution form than slightly increased in viscosity below 25° C. When the sample was analyzed at fixed temperature and different shear rates, shear thinning behavior showed at 25° C. and 37° C. There was no significant change observed in the viscosity at 4° C. and 16° C. that showed Newtonian flow behavior. This data is supporting that thereto reversible gel formulation will be in solution form below 25° C. At refrigerating temperatures (2-8° C.) for complete formulation TFR loaded nanoparticles was suspended in citrate buffed solution (pH 4.2) at lower temperature it showed white suspension. Partial settling of nanoparticles was observed at storage and after shaking well it was re-suspended.

In vitro release of TFR in SVF conducted for 8 and 24 h. 15% of the drug was released in the first 30 min and this can be attributed to the burst TFR release from the outer gel matrix. In 8 h, cumulative % drug release was 61% and after 24 h it was 67.75%. In vitro release data clearly indicated a sustained TFR release profile. Drug Release kinetics (zero order, first order, and Higuchi model) were fitted to the release profile and correlation (R2) values obtained were, (0.85, 0.96, and 0.98 respectively).

Both preparation methods were found efficient to prepare PLGA nanoparticles. Results revealed that emulsification-solvent evaporation method has advantage over the solvent diffusion method for encapsulation of TNF but particles size was increased as compare to solvent diffusion method. Thermoreversible solution dispersed TNF loaded PLGA nanoparticles was in solution form at 2-8° C. temperature and have capability to converted to gel matrix at ≥25° C. temperature. Sustained drug release behavior was showed by in-vitro release data and drug release mechanism was diffusion and erosion controlled. This study suggested that possibility of this formulation for vaginal drug delivery of anti HIV drugs. Research studies are in progress to improve the drug encapsulation efficiency of TFR nanoparticles, assess the long-term formulation stability and test the anti-HIV efficacy of the formulation. Additionally, it is required to generate toxicity and safety data.

It should be appreciated that an HIV drug, such as tenofovir, may be administered with an efflux transporter inhibitor, and/or in the form of nanoparticles, and/or in the form of a mucosal gel.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A method for increasing the bioavailability of an HIV drug in a subject, the method comprising the step of:
   administering a therapeutically effective amount of a carrier, an HIV drug and an efflux transporter inhibitor to the subject, the efflux transporter inhibitor administered in an amount effective to reduce the efflux of the HIV drug through the subject's T-cells as compared to using the same HIV drug in the same amount but without the efflux transporter inhibitor, wherein the HIV drug is Tenofovir and the efflux transporter inhibitor is selected from the group consisting of MK571, Pgp-4008, Fumitrimorgin C, and combinations thereof.

2. The method according to claim 1, wherein the HIV drug and efflux transporter inhibitor are topically applied together as a mucosal gel.

3. The method according to claim 1, wherein the efflux transporter inhibitor and HIV drug are administered at substantially the same time.

4. The method according to claim 1, wherein the efflux transporter inhibitor is administered in an amount of about 1 µM to about 1 mM.

5. The method according to claim 1, wherein a ratio of the efflux transporter inhibitor to the HIV drug is about 1:1 to about 1:100.

6. The method according to claim 1, wherein the efflux transporter inhibitor is administered in an amount effective to increase the bioavailability of the HIV drug by at least 50% as compared to using the same HIV drug in the same amount but without the efflux transporter inhibitor.

7. A composition for increasing the bioavailability of an HIV drug in a subject, the composition comprising:
   a HIV drug;
   an efflux transporter inhibitor; and
   a carrier, the efflux transporter inhibitor being present in an amount effective to reduce the efflux of the HIV drug in the subject's T-cells as compared to using the same HIV drug in the same amount but without the efflux transporter inhibitor.

8. The composition according to claim 7, wherein composition is in the form of a mucosal gel.

9. The composition according to claim 7, wherein the efflux transporter inhibitor is in an amount of about 1 µM to about 1 mM.

10. The composition according to claim 7, wherein a ratio of the efflux transporter inhibitor to the HIV drug is about 1:1 to about 1:100.

11. The composition according to claim 7, wherein the efflux transporter inhibitor is in an amount effective to increase the bioavailability of the HIV drug by at least 50% as compared to using the same HIV drug in the same amount but without the efflux transporter inhibitor.

12. A method for increasing the bioavailability of an HIV drug in a subject, the method comprising the step of:

administering a therapeutically effective amount of a carrier, an HIV drug and an efflux transporter inhibitor to the subject, the efflux transporter inhibitor administered in an amount effective to reduce the efflux of the HIV drug through the subject's T-cells as compared to using the same HIV drug in the same amount but without the efflux transporter inhibitor, wherein the HIV drug and efflux transporter inhibitor are topically applied as a mucosal gel and the HIV drug is Tenofovir encapsulated in nanoparticles, and the efflux transporter inhibitor is selected from the group consisting of MK571, Pgp-4008, Fumitrimorgin C, and combinations thereof.

* * * * *